(12) United States Patent
Julius et al.

(10) Patent No.: US 6,582,485 B1
(45) Date of Patent: Jun. 24, 2003

(54) FUEL AND LUBRICANT ADDITIVES

(75) Inventors: Manfred Julius, Limburgerhof (DE); Roland Ettl, Hassloch (DE); Wolfgang Günther, Mettenheim (DE); Thomas Greindl, Bad Dürkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/667,862

(22) Filed: Sep. 22, 2000

Related U.S. Application Data

(62) Division of application No. 09/125,375, filed on Aug. 17, 1998, now Pat. No. 6,165,237.

(30) Foreign Application Priority Data

Feb. 23, 1996 (DE) .......................... 196 06 846
Feb. 23, 1996 (DE) .......................... 196 06 845

(51) Int. Cl.$^7$ .......................... C10L 1/22; C10M 149/08
(52) U.S. Cl. .......................... 44/384; 508/558; 558/452
(58) Field of Search .......................... 44/384; 508/558; 558/452

(56) References Cited

U.S. PATENT DOCUMENTS 4,058,469 A * 11/1977 Hoke .......................... 508/447
5,492,641 A * 2/1996 Mohr .......................... 558/408

* cited by examiner

Primary Examiner—Cephia D. Toomer
(74) Attorney, Agent, or Firm—Keil & Weinkauf

(57) ABSTRACT

Compounds of the general formula I $$Z\text{—}CH_2\text{—}NY_{2-n}H_n \quad (I)$$

where n is 0 or 1,

Z is a straight-chain or branched polyalkyl radical having a number average molecular weight of from about 150 to 40,000, and Y is a radical of the formula IIa or IIb

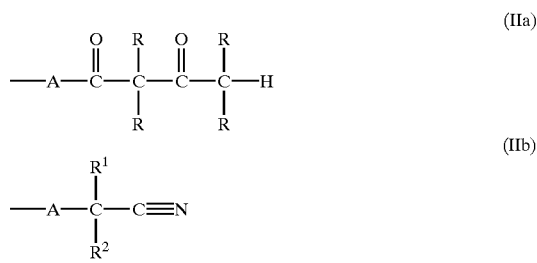

where the radicals R, $R^1$ and $R^2$ independently of one another, are each hydrogen, an unsubstituted or substituted alkyl, alkenyl or alkynyl radical or an unsubstituted or substituted cycloalkyl, aryl or arylalkyl radical, which may carry one or more heteroatoms, and A is an alkyleneimine radical; or, if n is 0, one of the radicals Y may be a polyoxyalkylene radical, and processes for their preparation and fuel and lubricant compositions, and mixtures of additives, which contain the novel compounds.

16 Claims, No Drawings

FUEL AND LUBRICANT ADDITIVES

This application is a division of U.S. Ser. No. 09/125,375, filed Aug. 17, 1998, now U.S. Pat. No. 6,165,237.

The present invention relates to novel derivatized polyalkylamine additives for fuels and lubricants, processes for the preparation of these additives and fuels and lubricants and additive concentrates which contain these novel additives.

Carburettors and intake systems of gasoline engines as well as injection system for fuel metering in gasoline and diesel engines are becoming contaminated with impurities to an increasing extent. The impurities are the result of dust particles from the air taken in by the engine, uncombusted hydrocarbon residues from the combustion chamber and the vent gases from the crank case which are passed into the carburettor.

These residues shift the air/fuel ratio during idling and in the lower part-load range so that the mixture becomes richer and the combustion more incomplete. As a result of this, the proportion of uncombusted or partially combusted hydrocarbons in the exhaust gas and the benzene consumption increase.

It is known that these disadvantages can be avoided by using fuel additives for keeping valves and carburettor or intake systems clean (cf. for example: M. Rossenbeck in Katalysatoren, Tenside, Mineralöladditive, Ed. J. Falbe, U. Hasserodt, pp. 223, G. Thieme Verlag, Stuttgart 1978). Depending on the mode of action and preferred place of action of such detergent additives, a distinction is now made between two generations. The first generation of additives was only able to prevent the formation of deposits in the intake system, not to remove existing deposits. On the other hand, additives of the second generation can prevent and eliminate deposits (keep-clean and clean-up effect). This is permitted in particular by their excellent heat stability in zones of relatively high temperature, in particular in the intake valves.

The molecular structural principle of these additives of the second generation which act as detergents is based on the linkage of polar structures to generally relatively high molecular weight, nonpolar or oleophilic radicals. Typical members of the second generation of additives are products based on polyisobutene in the nonpolar moiety, in particular additives of the polyisobutylamine type.

Such detergents can be prepared by two different multistage synthesis processes, starting from polyisobutenes.

The first process involves chlorination of the polymeric parent structure, followed by nucleophilic substitution of the polymeric parent structure by amines or, preferably, ammonia. The disadvantage of this process is the use of chlorine, which results in the occurrence of chlorine- or chloride-containing products, which is not at all desirable today.

In the second process, the polyisobutylamines are prepared starting from polyisobutene, by hydroformylation and subsequent reductive amination according to EP 0 244 616.

If ammonia is used in the reductive amination in the second process, the reaction products of the ammonia usually display excellent efficiency with regard to keeping valves and carburettors clean, but they are at best neutral in their action on an engine lubricant, in particular with regard to their oil sludge-dispersing actions.

Additives which are particularly advantageous from the technical and economic point of view are therefore those which simultaneously combine the properties of detergents and dispersants and are obtainable by simple, chlorine-free synthesis processes.

Such additives are disclosed in EP 0 568 873. The latter describes β-aminonitriles of the formula

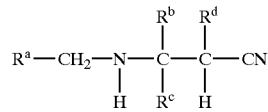

where $R^a$ is an aliphatic hydrocarbon radical having alkyl side groups and an average molecular weight of from 250 to 5,000 and $R^b$, $R^c$ and $R^d$, independently of one another, are each hydrogen or $C_1$–$C_8$-alkyl or $R^b$ and $R^d$ are each phenyl, and the corresponding N-alkyl-1,3-propylenediamine obtained by hydrogenation.

There is, however, an additional demand for further chlorine-free additive components in order to be able better to adapt the additives to the requirements of the respective application.

It is the object of the present invention to provide further compounds which are suitable as fuel and lubricant additives and are obtained by chlorine-free synthesis.

We have found that this object is achieved by providing derivatives of long-chain amines which are obtained by functionalization of the amine group by a cyanomethylation or by reaction with diketenes. For the purpose of the present invention, cyanomethylation is the linking of a cyanoalkyl group by its α-carbon atom to an amine nitrogen.

The present invention relates in particular to compounds of the general formula I

where n is 0 or 1,

Z is a straight-chain or branched polyalkyl radical having an average molecular weight of from about 150 to 40,000, Y is a radical of the formula IIa or IIb

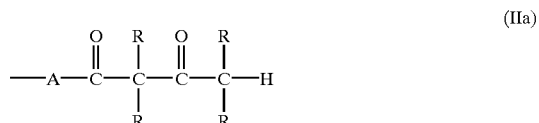

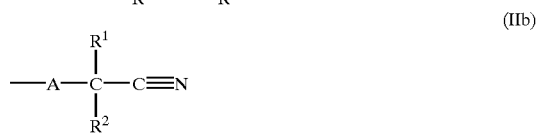

where

R, $R_1$ and $R_2$ are identical or different and, independently of one another, are selected from the group consisting of hydrogen, unsubstituted and substituted alkyl, alkenyl and alkynyl radicals and unsubstituted and substituted cycloalkyl, aryl and arylalkyl radicals which may contain one or more heteroatoms; and A is an alkyleneimine radical of the formula III $$\left[ Alk-\underset{R^3}{N} \right]_m \quad \text{(III)}$$

where
m is an integer from 0 to 10;
Alk is straight-chained or branched, unsubstituted or substituted alkylene;
$R^3$ is hydrogen, alkyl, alkenyl, alkynyl, aryl or, if Y is a radical of formula IIA, a keto radical of the formula IVa $$-\underset{}{\overset{O}{\underset{\|}{C}}}-\underset{R}{\overset{R}{\underset{|}{C}}}-\underset{}{\overset{O}{\underset{\|}{C}}}-\underset{R}{\overset{R}{\underset{|}{C}}}-H \quad \text{(IVa)}$$

where
R has the above mentioned meanings;
or, if Y is a radical of formula IIb, a cyano radical of the formula IVb $$-\underset{R^2}{\overset{R^1}{\underset{|}{C}}}-C\equiv N \quad \text{(IVb)}$$

where
$R^1$ and $R^2$ have the above-mentioned meanings; or, if n is O, one of the radicals Y may be a polyoxyalkylene radical of the formula (V)

$$-[Alk-O]_q-E \quad \text{(V)}$$

where
q is an integer from 1 to 30,
Alk is as defined above and
E is hydrogen or $C_1$–$C_6$-alkyl.

According to a first preferred embodiment the present invention relates to cyanomethylated compounds of the formula I, where Z and n have the above-mentioned meanings and Y is a radical of the formula IIc $$\left[ \left( \underset{R^5}{\overset{R^4}{\underset{|}{C}}} \right)_p - \underset{R^3}{N} \right]_m - \underset{R^2}{\overset{R^1}{\underset{|}{C}}}-C\equiv N \quad \text{(IIc)}$$

where
$R^1$, $R^2$, $R^3$ and m have the above-mentioned meanings,
$R^4$ and $R^5$ are identical or different and have the meanings stated above for $R^1$ and $R^2$, and
p is an integer from 2 to 5.

More preferred cyanomethylated additives are compounds of the formula I, where

Z, m, n and p have the above-mentioned meanings,
$R^1$ and $R^2$, independently of one another, are selected from the group consisting of hydrogen and alkyl, in particular $C_1$–$C_{10}$-alkyl,
$R^3$ is hydrogen, alkyl, in particular $C_1$–$C_{10}$-alkyl, or a cyano radical of the formula IVb, and
$R^4$ and $R^5$, independently of one another, are each hydrogen or $C_1$–$C_6$-alkyl.

Particularly preferred additives are those in which Z is a radical composed of isobutene units and having a number average molecular weight of about 800–1500, n is 0 or 1 and Y is a group of the formula $$-CR^1R^2-CN$$

where $R^1$ and $R^2$ independently of one another, are each hydrogen or $C_1$–$C_{10}$-alkyl.

According to another preferred embodiment the present invention relates in particular to diketene derivatives of the general formula Ia $$Z-CH_2-N \begin{cases} \overset{O}{\underset{\|}{C}}-\underset{R}{\overset{R}{\underset{|}{C}}}-\overset{O}{\underset{\|}{C}}-\underset{R}{\overset{R}{\underset{|}{C}}}-H \\ \left[ \overset{O}{\underset{\|}{C}}-\underset{R}{\overset{R}{\underset{|}{C}}}-\overset{O}{\underset{\|}{C}}-\underset{R}{\overset{R}{\underset{|}{C}}}-H \right]_n \end{cases} \quad \text{(Ia)}$$

where Z, R and n have the above-mentioned meanings.

The radicals R, independently of one another, are preferably each hydrogen, a straight-chain or branched, unsubstituted or substituted $C_1$–$C_{30}$-alkyl, $C_2$–$C_{30}$-alkenyl or $C_2$–$C_{30}$-alkynyl radical or an unsubstituted or substituted $C_3$–$C_8$-cycloalkyl, phenyl, naphthyl or phenyl-$C_1$–$C_{12}$-alkyl or naphthyl-$C_1$–$C_{12}$-alkyl radical, which may carry one or more heteroatoms.

Compounds of the formula Ia, where Z has a number average molecular weight of from about 800 to 1500, n is 0 or 1 and radicals R are identical and selected from hydrogen and $C_1$–$C_{30}$-alkyl are particularly preferred.

The polyalkyl radical Z in compounds of the general formula (I) is preferably obtained by homo- or copolymerization of straight-chain or branched $C_2$–$C_{30}$-alkenes, preferably $C_2$–$C_6$-alkenes, particularly preferably $C_2$–$C_4$-alkenes. Particularly preferred $C_2$–$C_4$-alkenes are 1-alkenes, such as propylene, 1-butene and isobutene. For example, Z may be derived from a copolymer of 1-butene and isobutene, and Z may likewise have an average molecular weight of from about 800 to about 1500.

Alkyl radicals which may be used according to the invention are straight or branched, saturated hydrocarbon chains of 1 to 30 carbon atoms. Examples are $C_1$–$C_6$-alkyl, such as methyl, ethyl, n-propyl, iso-propyl, n-butyl, sec-butyl, iso-butyl, tert-butyl, n-pentyl, sec-pentyl, iso-pentyl, n-hexyl or 1-, 2- or 3-methylpentyl, long-chain alkyl radicals, such as straight-chain heptyl, octyl, nonyl, decyl, undecyl, lauryl, tridecyl, myristyl, pentadecyl, palmityl, heptadecyl, stearyl, nonadecyl, arachinyl, behenyl, lignoceryl, ceryl and myricyl, and the singularly or multiply branched analogues thereof. Preferred long-chain radicals are lauryl, myristyl, palmityl, stearyl and arachinyl.

Alkenyl radicals which may be used according to the invention are straight or branched hydrocarbon chains having at least one carbon-carbon double bond and having 2 to 30 carbon atoms. Examples of mono unsaturated $C_2-C_{30}$-alkenyl radicals are $C_2-C_6$-alkenyl radicals such as vinyl, allyl, 1-propenyl, isopropenyl, 1-, 2- or 3-butenyl, methallyl, 1,1-dimethylallyl, 1-, 2-, 3-, 4- or 5-hexenyl, long-chain radicals, such as straight-chain heptenyl, octenyl, nonenyl, decenyl, undecenyl, dodecenyl, tridecenyl, pentadecenyl, palmitoleyl, icosenyl and triacontenyl, and the branched analogues thereof, where the double bond may occur in any desired position. According to the invention, both the cis and the trans isomers of the above $C_2-C_{30}$-alkenyl radicals are included. A preferred mono unsaturated long-chain radical is oleyl.

Alkynyl radicals which may be used according to the invention are straight or branched hydrocarbon chains having at least one carbon-carbon triple bond and 2 to 30 carbon atoms. Examples include ethinyl, 1- or 2-propinyl, 1-, 2- or 3-butinyl and the corresponding alkynyl analogues of the above-mentioned alkenyl radicals.

Cycloalkyl radicals which may be used according to the invention include $C_3-C_8$-cycloalkyl radicals such as cyclopropyl, cyclobutyl, cyclopentyl, cyclohexyl, cycloheptyl, cyclooctyl, cyclopropylmethyl, cyclopropylethyl, cyclopropylpropyl, cyclobutylmethyl, cyclobutylethyl, cyclopentylethyl, cyclopentylpropyl and the like.

Examples of aryl radicals which may be used according to the invention are phenyl and naphthyl.

Arylalkyl radicals which may be used according to the invention are in particular phenyl-$C_1-C_{10}$-alkyl and naphthyl-$C_1-C_{10}$-alkyl, the $C_1-C_{10}$-alkyl moiety being as defined above.

The cycloalkyl, aryl and arylalkyl groups which may be used according to the invention may, if required, contain 1 or more, for example 1 to 4, heteroatoms, such as O, S and N, oxygen and nitrogen being preferred as heteroatoms. Examples of cyclic heteroalkyl radicals are tetrahydrofuranyl, piperidinyl, piperazinyl and morpholinyl. Examples of heteryl groups are 5- or 6-membered aromatic ring systems which comprise from 1 to 4 of the stated heteroatoms, eg. furyl, pyrrolyl, imidazolyl, pyrazolyl, oxazolyl, isoxazolyl, oxadiazolyl, tetrazolyl, pyridyl, pyrimidinyl, pyrazinyl, pyradizinyl, triazinyl, tetrazinyl and the like.

Straight-chain or branched alkylene radicals which may be used according to the invention include straight-chain $C_1-C_{10}$-alkylene radicals, eg. ethylene, propylene, butylene, pentylene and hexylene, and branched $C_1-C_{10}$-alkylene radicals, eg. 1,1-dimethylethylene, 1,3-dimethylpropylene, 1-methyl-3-ethyl-propylene, 2,3-dimethylbutylene, 1,3-dimethylbutylene, 1,1-dimethylbutylene, 1,2-dimethylpentylene and 1,3-dimethylhexylene.

Examples of substituents which are suitable according to the invention are $C_1-C_6$-alkyl, $C_1-C_6$-alkoxy, $C_2-C_6$-alkenyl, $C_1-C_6$-alkanoyl, such as acetyl and propionyl, nitro and amino.

The present invention furthermore relates to a process for the preparation of compounds of the general formula (I), wherein a polyalkylamine of the general formula VI

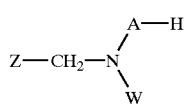

(VI)

where

Z has the above-mentioned meanings,

W is hydrogen or —A—H, and

A is an alkyleneimine radical of the formula VII

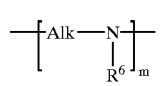

(VII)

where Alk and m have the above-mentioned meanings and $R^6$ is hydrogen, straight-chain or branched alkyl, alkenyl or alkynyl or aryl, either a$_1$) is reacted with at least one diketene of the formula IX

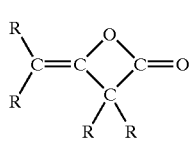

(IX)

where R has the above mentioned meanings, in an inert solvent, in order to obtain a compound of formular I, where in at least one radical Y is of formula IIa, or a$_2$) is reacted with hydrocyanic acid or a salt thereof and least one compound of the general formula VIII

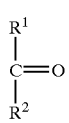

(VIII)

where $R^1$ and $R^2$ have the above-mentioned meanings in order to obtain a compound of formula I wherein at least one radical Y is of formula IIb.

The reaction a$_2$) preferably is carried out in an aqueous medium in the presence of a phase-transfer catalyst.

If, in the reaction product obtained, according to a$_1$) or a$_2$) W is hydrogen, this can, if desired, be substituted in a conventional manner by a group of the formula V

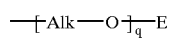

(V)

where Alk, E and q have the above-mentioned meanings.

The derivatization of the polyalkylamines with diketenes according to process a$_1$) to give the novel diketene-derivatized compounds is carried out in a manner known per se by adding the diketene to the polyalkylamine in the absence of a solvent or in an inert solvent, while cooling, at room temperature or at elevated temperatures, depending on the reactivity of the reactants. Examples of suitable solvents include sulfur- and chlorine-free solvents, such as relatively high-boiling hydrocarbons, eg. n-hexane, n-octane, n-decane or isododecane, or dipolar aprotic solvents, such as anhydrous tetrahydrofuran. The polyalkylamine is preferably dissolved in a suitable solvent, and the diketene, if necessary dissolved in the same solvent, is added dropwise while stirring. The reaction products obtained can be used without further purification, if necessary after distilling off the solvent or removing excess reagents.

According to the prior art, the cyanomethylation of amine is usually carried out by the "Strecker-Synthesis" (cf. for example: Strecker, Ann. Chem. 75, (1850), 27; Kendall, McKenzie, Org. Synth., 9, (1929), 4; H. Bucherer, A. Grolee, Chem. Ber. 39, (1906), 992; E. Knoevenagel, Chem. Ber. 37, (1904), 402; DE 2 107 757; DE 2 624 891) by reacting the amine with aqueous formaldehyde and hydrocyanic acid. Reaction of polyisobuteneamines of the above formula VI with hydrocyanic acid or salts of hydrocyanic acid and formaldehyde or paraformaldehyde does not lead to the desired reaction, even with the addition of solubilizers. Surprisingly, however, it was found, according to the invention, that the novel cyanomethylated additives can be prepared according to process $a_2$) in surprisingly good yield by adding a phase-transfer catalyst.

The nucleophilic substitution of halogenated hydrocarbon compounds with sodium cyanide under phase-transfer catalysis is generally known (C. M. Starks, J. A. Chem. Soc. 93, (1971), 195), as is the hydrocyanation of carbonyl compounds with the phase-transfer catalysts (C. L. Liotta, A. M. Dabdoub and L. H. Zalkow, Tetrahedron Lett., (1977), 1117). However, the use of phase-transfer catalysts in the cyanomethylation of hydrophobic amines is novel. It is surprising that the reaction is accelerated although formaldehyde is added in an aqueous solution.

Suitable phase-transfer catalysts for carrying out the novel process $a_2$) include quaternary ammonium and phosphonium salts, although quaternary ammonium salts are preferred. Examples of phase-transfer catalysts which may be used are benzyltriethylammonium chloride, tetrabutylammonium bromide, methyltricaprylammonium chloride and methyltributylammonium chloride and the corresponding halogen-free forms of these compounds.

The novel preparation process $a_2$) is preferably carried out by a procedure in which the polyalkylamine of the formula VI is dissolved in a suitable solvent, eg. tetrahydrofuran or another dipolar aprotic solvent, and the phase-transfer catalyst is added to the solution. An aqueous cyanide solution in which the ketone compound of the formula VIII has been dissolved is then added. The reaction mixture is heated to about 40–70° C. and the pH of the solution is kept at about 8–9. After the end of the reaction, the organic phase is separated off and the desired additive is isolated therefrom.

If mixtures of ketone compounds of the general formula VIII are used in the novel preparation process, the novel additives simultaneously contain different terminal cyano groups of the formula IIb.

The polyalkylamines of the general formula VI can be prepared by hydroformylation of reactive polyalkenes and subsequent reductive amination of the oxo product. The reactive polyalkenes having an average molecular weight of from about 150 to 40,000 are homo- or copolymers of straight-chain or branched $C_2$–$C_{30}$-alkenes, preferably $C_2$–$C_6$-alkenes, in particular $C_2$–$C_4$-alkenes. Reactive polyalkenes include unsaturated polymers of high chemical homogeneity, more than 10% of the double bonds being in the alpha position. A possible method for the preparation of reactive polyalkenes is disclosed in DE 27 02 604. Particularly preferred reactive polyalkenes are those which are prepared from 1-alkenes, in particular propylene, 1-butene, isobutene or mixtures thereof.

Other suitable polyalkylamines of the general formula VI are amines according to EP 0 244 616 and EP 0 695 338, the content of which is hereby incorporated by reference. EP 0 244 616 describes in particular polyalklamines in which Z is derived from isobutene and up to 20% by weight of n-butene, it being possible for the molecular weight of the polyisobutene radical to be from about 300 to about 5000. EP 0 695 338 describes in particular polyalkylamines in which Z is derived from one or more 1-n-alkenes of 3 to 6 carbon atoms and up to 50-% by weight of ethene, it being possible for Z to have about 20–400 carbon atoms.

However, an important criteria for all polyalkylamines which may be used according to the invention is that they contain at least one primary or secondary amine group which can be derivatized by cyanomethylation or by reaction with diketenes, as described above.

Additives particularly preferred according to the invention are those which are prepared starting from polybutylamines and polyisobutylamines of the formula VI and which are disclosed in EP 0 244 614.

The present invention furthermore relates to lubricant compositions which contain at least one novel polyalkylamine derivative according to the above definition, if necessary in combination 40 with further conventional lubricant additives. Examples of conventional additives are corrosion inhibitors, antiwear additives, viscosity improvers, detergents, antioxidants, antifoams, lubricacy improvers and pour point improvers. The novel compounds are usually present in amounts of from about 1 to 15, preferably from about 0.5 to 10% by weight, based on the total weight of the composition.

Examples of lubricants prepared according to the invention include oils and greases for motor vehicles and industrially used drive assemblies, in particular engine oils, gear oils and turbine oils.

The present invention furthermore relates to fuel compositions, for example fuels for gasoline and diesel engines, which contain the novel additives. The novel compounds serve therein in particular as detergents for keeping the fuel intake system clean. Owing to their dispersing properties, they have an advantageous effect on the engine lubricant, which they can enter during operation.

To test the novel products with regard to their dispersant properties, it is possible to use a spot test, as described, for example by A. Schilling in "Les Huiles pour Moteurs et la Graissage des Moteurs", Vol. 1, 1962, page 89 et seq., in a somewhat modified form.

The novel polyalkylamine derivatives are metered into commercial fuels in a concentration of from about 20 to 5000, preferably from about 50 to 1000, mg/kg of fuel. The novel additives can, if required, also be added together with other known additives.

While novel additives in which Z has a number average molecular weight of about 2000–40,000 are preferably used in lubricant compositions, compounds in which Z has a number average molecular weight of about 150–5000, preferably about 500–2500, and in particular about 800–1500, are particularly useful for use as fuel additives.

Finally, the present invention relates to additive mixtures which, in concentrated form, contain at least one novel compound in combination with other fuel additives, in particular detergents and dispersants. A combination with, for example, polyisobutylamines disclosed in U.S. Pat. No. 4,832,702 is particularly preferred.

In principle, any known product from among the products suitable for this purpose, may be used as a detergent component in the novel additive mixtures, said products being described, for example, in J. Falbe, U. Hasserodt, Katalysatoren, Tenside und Mineralöladditive, G. Thieme Verlag, Stuttgart, 1978, page 221 et seq., or in K. Owen, Gasoline and Diesel Fuel Additives, John Wiley & Sons 1989, page 23 et seq.

N-containing detergents, for example compounds which contain an amino or amido group, are preferably used. Polyisobutylamines according to EP 0 244 616, ethylenediaminetetraacetamides and/or ethylenediaminetetraacetimides according to EP 0 188 786 or polyetheramines according to EP 0 356 725 are particularly suitable, and reference may be made to the definitions in these publications. Owing to their method of preparation, the products described there likewise have the advantage of being chlorine- or chloride-free.

On the other hand, these additives may also be combined with carrier oils. In particular, carrier oils based on polyalkylene glycol, for example corresponding ethers and/or esters, as described in U.S. Pat. No. 5,004,478 or DE 38 38 918 A1, are suitable. Polyoxalkylenemonooles having terminal hydrocarbon groups (U.S. Pat. No. 4,877,416) or carrier oils as disclosed in DE 41 42 241 may also be used.

The examples which follow illustrate the present invention.

EXAMPLE 1

Preparation of Cyanomethylated Polyisobuteneamine 250 g of polyisobuteneamine ($M_w$ about 1000) are mixed with 125 g of tetrahydrofuran and 250 g of water, and 55 g of formaldehyde (30% strength) are added. After addition of 0.57 g of benzyltriethylammonium chloride and 81.7 g of 33% strength aqueous sodium cyanide solution, the pH of the aqueous solution is brought to about 9 with 56 g of 50% strength aqueous sulfuric acid. While stirring vigorously, the pH is kept at 8–9 for 2 hours at 60° C. by adding a total of 14 g of 15% strength aqueous sodium hydroxide solution. After this time, the conversion is 89%, based on unconverted cyanide. After cooling, the supernatant organic phase is separated off and extracted twice by shaking with 300 g of water. After the solvent has been stripped off under reduced pressure, 244 g of a highly viscose product remain, corresponding to 90% of theory. A mixture of unsubstituted, monosubstituted and disubstituted polyisobuteneamine is obtained, the determination being based on NMR and mass spectrometry.

EXAMPLE 2 (Comparative Example)

a.) 110 g of 30% strength aqueous formaldehyde and 30 g of hydrocyanic acid are added dropwise in succession at 20° C. to a solution of 500 g of polyisobuteneamine in 1.5 l of tetrahydrofuran. This mixture is stirred for 35 hours at 60° C.; after this time, the conversion is <20%, based on unconverted cyanide. After the organic phase has been separated off and the solvent distilled off, only unconverted polyisobuteneamine is obtained.

b.) 15 g of hydrocyanic acid are added dropwise at 20° C. to a solution of 250 g of polyisobuteneamine in 100 g of tetrahydrofuran, and a solution of 22.5 g of trioxane in 50 g of tetrahydrofuran is subsequently added dropwise in the course of 1 hour at the same temperature. After a total of 30 hours at 60° C., the solvent is removed; according to NMR analysis, polyisobuteneamine having a degree of substitution of <20% remains.

EXAMPLE 3

Reaction of Polyisobutylamine (PIBA) With Distearyl Diketene

An equimolar amount of distearyl diketene (0.4 mol) was added in the course of 20 minutes to a solution of 0.4 mol of PIBA (PIBA prepared according to EP 0 244 616, MW~1041) in isododecane at 40° C. The solution thus obtained was stirred for a further 30 minutes at 40° C. and then cooled to the room temperature. A colorless liquid was obtained.

Yield: quantitative; IR (Film, cm$^{-1}$): 3300 (N—H); 2950; 2925; 2845; 1705 (C=O); 1630 (O=C—NH—); 1455; 1390; 1350; 1220.

EXAMPLE 4

Reaction of Polyisobutylamine With Distearyl Diketene 0.4 mol of PIBA (PIBA prepared according to EP 0 244 616, MW~1041) was heated to 60° C. 0.4 mol of distearyl diketene was then slowly added. After the end of the addition, the reaction mixture was stirred for a further 45 minutes and then cooled to room temperature. A colorless, viscous oil was obtained.

Yield: quantitative;

IR (Film, cm$^{-1}$): 3300 (N—H) ; 2950; 2925; 2845; 1705 (C=O); 1630 (O=C—NH—); 1455; 1390; 1350; 1220.

EXAMPLE 5

Reaction of PIBA With Dioleyl Diketene

A solution of 0.4 mol of PIBA (PIBA prepared according to EP 0 244 616, MW~1041) in isododecane at 30° C. was initially taken. 0.4 mol of dioleyl diketene was slowly added dropwise with vigorous stirring. After the end of the addition, the solution was stirred for a further 45 minutes. A pale yellow liquid was obtained.

Yield: quantitative; IR (Film, cm$^{-1}$): 3300 (N—H); 2950; 2925; 2845; 1705 (C=O); 1630 (O=C—NH—); 1455; 1390; 1350; 1220.

EXAMPLE 6

Reaction of Polyisobutylamine (PIBA) With Diketene

A solution of 17.6 g (0.21 mol) of diketene in 100 ml of tetrahydrofuran was added dropwise in the course of one hour to a solution of 207.8 g (0.20 mol) of polyisobutylamine (PIBA prepared according to EP 0 244 616, MW~1041) in 1000 ml of anhydrous tetrahydrofuran at 0° C. while stirring. The reaction was slightly exothermic. The stirring process was continued for a further two hours at 0° C. Thereafter, the solvent was distilled off and remaining traces of tetrahydrofuran and diketene were removed at 50° C. and 0.5 mbar. 222.0 g (0.197 mol) of N-acetoacetyl-polyisobutylamine remained behind as a slightly yellowish viscous oil.

Yield: virtually quantitative; Amine number: 0; IR (Film, cm$^{-1}$): 2950, 1650, 1470, 1390, 1365, 1230; $^{13}$C-NMR (100 MHz, CDCl$_3$, extract): δ=22.70 (q, CH—C̲H$_3$), 29.54 (q, H$_3$C̲—C=O), 37.75 (t, C̲H$_2$—CH$_2$—N), 49.51 (t, C̲H$_2$—CO—CH$_3$), 165.11 (HN—C̲=O), 204.76 (H$_3$C—C̲=O), 31.24 (q), 38.15 (s), 59.70 (t) (polyisobutyl). For comparison: $^{13}$C-NMR of the PIBA used (100 MHz, CDCl$_3$, extract): δ=23.06 (CH—C̲H$_3$), 26.55 (C̲H—CH$_3$), 40.27 ( C̲H$_2$—NH$_2$), 44.14 (C̲H$_2$—CH$_2$—NH$_2$); 31.32 (q), 38.17 (s), 59.56 (t) (polyisobutyl).

EXAMPLE 7

Engine Test for Testing the Action as Intake System Cleaner

Testing the products of the present invention as fuel additives, in particular with regard to their suitability of the present invention as intake system cleaners, is carried out with the aid of engine tests which are performed in test bed trials with a 1.2 l Opel Kadett engine according to CEC F/04/A/87. Fuel used: European premium-grade unleaded. The results are summarized in table 1 below.

TABLE 1

| | | Reduction of deposits in the intake valve | | | | |
|---|---|---|---|---|---|---|
| Additive from example | Dose [mg/kg] | Valves | Intake valve deposits [mg]* | | | |
| | | | 1 | 2 | 3 | 4 |
| 1 | 200 | | 0 (554) | 12 (343) | 0 (293) | 6 (484) |
| 6 | 200 | | 3 (277) | 2 (175) | 2 (183) | 2 (337) |
| 3 | 200 | | 8 (554) | 4 (343) | 3 (293) | 5 (484) |

*Values in brackets: Deposits without the addition of an additive

We claim:

1. A process for the preparation of a compound having the formula I $$Z-CH_2-NY_{2-n}H_n \quad (I)$$

where
n is 0 or 1;
Z is a straight-chain or branched polyalkyl radical having an average molecular weight of from about 500 to 40,000;
Y is a radical of the formula IIb

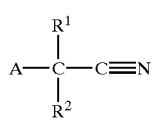
(IIb)

where
$R_1$ and $R_2$ are identical or different and are selected from the group consisting of hydrogen, unsubstituted and substituted alky, alkenyl and alkynyl radicals and unsubstituted and substituted cycloalkyl, aryl and arylalkyl radicals which optionally contains one or more heteroatoms; and
A is an alkyleneimine radical of the formula III

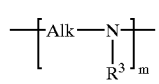
(III)

where
m is an integer from 0 to 10;
Alk is straight-chained or branched, unsubstituted or substituted alkylene;
$R^3$ is hydrogen, alkyl, alkenyl, alkynyl, aryl or, a cyano radical of the formula IVb

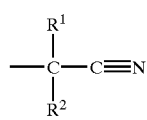
(IVb)

where $R^1$ and $R^2$ have the above-mentioned meanings; or, if n is 0, one of the radicals Y is optionally a polyoxyalkylene radical of the formula V

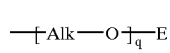
(V)

where
q is an integer from 1 to 30,
Alk is as defined above, and
E is hydrogen or $C_1$–$C_6$-alkyl.
wherein in the process
a) a polyalkylamine of the formula VI

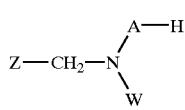
(VI)

where
Z has the above-mentioned meanings,
W is hydrogen or —A—H, and
A is an alkyleneimine radical of the formula VII

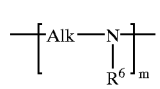
(VII)

where Alk and m have the above-mentioned meanings and $R^6$ is hydrogen, straight-chain or branched alkyl, alkenyl or alkynyl or aryl, is reacted with hydrocyanic acid or a salt thereof and at least one compound of the formula VIII

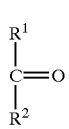
(VIII)

where $R^1$ and $R^2$ have the above mentioned meanings in order to obtain a compound of formula I, wherein at least one radical Y is of formula IIb; and
formula V

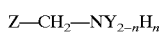
(V)

where Alk, E and p are as defined above.

2. A process as claimed in claim 1, wherein the reaction is carried out in an aqueous medium in the presence of a phase-transfer catalyst.

3. An additive for fuels or lubricants comprising a compound produced by a process as claimed in claim 1, and having the formula I $$Z-CH_2-NY_{2-n}H_n \quad (I)$$

where
n is 0 or 1;
Z is a straight-chain or branched polyalkyl radical having an average molecular weight of from about 500 to 40,000;

Y is a radical of the formula IIb

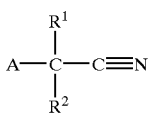
(IIb)

where
R$_1$ and R$_2$ are identical or different and are selected from the group consisting of hydrogen, unsubstituted and substituted alky, alkenyl and alkynyl radicals and unsubstituted and substituted cycloalkyl, aryl and arylalkyl radicals which optionally contains one or more heteroatoms; and
A is an alkyleneimine radical of the formula III

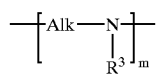
(III)

where
m is an integer from 0 to 10;
Alk is straight-chained or branched, unsubstituted or substituted alkylene;
R$^3$ is hydrogen, alkyl, alkenyl, alkynyl, aryl or, a cyano radical of the formula IVb

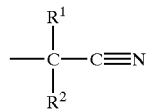
(IVb)

where R$^1$ and R$^2$ have the above-mentioned meanings; or, if
n is 0, one of the radicals Y is optionally a polyoxyalkylene radical of the formula V

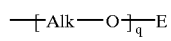
(V)

where
q is an integer from 1 to 30,
Alk is as defined above, and
E is hydrogen or C$_1$–C$_6$-alkyl.
4. A compound as claimed in claim 3, of the formula I, where Z and n have the above-mentioned meanings and Y is a radical of the formula IIc

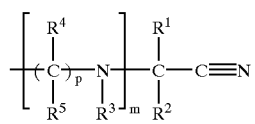
(IIc)

where
R$^1$, R$^2$, R$^3$, and m have the above mentioned meanings,
R$^4$ and R$^5$ are identical or different and have the meanings stated above for R$^1$ and R$^2$, and
p is an integer from 2 to 5.
5. A compound as claimed in claim 4, wherein Z m, n, and p have the above mentioned meanings, R$^1$ and R$^2$ are selected from the group consisting of hydrogen, and alkyl, R$^3$ is hydrogen, alkyl, in particular C$_1$–C$_{10}$-alkyl, or a cyano radical of the formula IVb, and
R$^4$ and R$^5$ are each hydrogen or C$_1$–C$_6$-alkyl.
6. A compound as claimed in claim 3, wherein Z is a polymer radical derived from at least one straight-chain or branched C$_2$–C$_{30}$-alkene.
7. A compound as claimed in claim 6, wherein the alkene is a 1-alkene.
8. A compound as claimed in claim 7, wherein the 1-alkene is selected from propylene, 1-butene and isobutene.
9. A compound as claimed in claim 8, wherein Z is derived from polybutene or polyisobutene or a copolymer of isobutene and up to 20% by weight of n-butene, and has an average molecular weight of from about 800 to about 1500.
10. A lubricant composition comprising one or more compounds as claimed in claim 3 in a total amount of about 1–15% by weight, based on the total weight of the composition, optionally in combination with further conventional lubricant additives.
11. A lubricant composition as claimed in claim 10, comprising at least one compound of the formula I, where Z has a number average molecular weight of from about 2000 to 40,000.
12. A fuel composition comprising one or more compounds as claimed in claim 3 in a total concentration of from about 20 to 5000 mg/kg of fuel, optionally in combination with further conventional fuel additives.
13. A fuel composition as claimed in claim 12, comprising at least one compound of the formula I, where Z has a number average molecular weight of from about 500 to 2500.
14. A additive mixture for fuels or lubricants, comprising one or more compounds as claimed in claim 3, optionally in combination with further conventional additive components.
15. The compound of claim 3 wherein R$^1$ is C$_1$–C$_{10}$-alkyl.
16. An additive for fuels or lubricants comprising a compound of the formula I

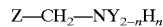
(I)

where
n is 0 or 1;
Z is a straight-chain or branched polyalkyl radical having an average molecular weight of from about 500 to 40,000;
Y is a radical of the formula IIb

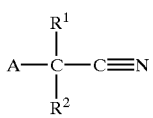
(IIb)

where
A is an alkyleneimine radical of the formula III

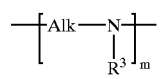
(III)

where
m is an integer from 0 to 10;
Alk is straight-chained or branched, unsubstituted or substituted alkylene;
R$^1$ and R$^2$ are identical or different and are selected from the group consisting of unsubstituted and substituted alkenyl and alkynyl radicals and unsubstituted and substituted cycloalkyl and arylalkyl radicals with optionally contain one or more heteroatoms, or if m is greater than 0, $R^1$ and $R^2$ are optionally selected from the group consisting of hydrogen, unsubstituted and substituted alkyl radicals and unsubstituted and substituted aryl radicals which optionally contain one or more heteroatoms; and $R^3$ is hydrogen, alkyl, alkenyl, alkynyl, aryl or, a cyano radical of the formula IVb

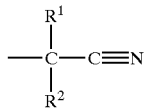 (IVb)

where $R^1$ and $R^2$ have the above-mentioned meanings; or, if n is 0, one of the radicals Y is optionally a polyoxyalkylene radical of the formula IV

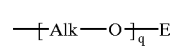 (V)

where q is an integer from 1 to 30,

Alk is as defined above and

E is hydrogen or $C_1$–$C_6$-alkyl.

* * * * *

UNITED STATES PATENT AND TRADEMARK OFFICE
CERTIFICATE OF CORRECTION

PATENT NO. : 6,582,485 B1
DATED : June 24, 2003
INVENTOR(S) : Julius et al.

It is certified that error appears in the above-identified patent and that said Letters Patent is hereby corrected as shown below:

Column 11,
Line 26, "or1" should be -- or 1 --.

Column 15,
Lines 1 and 2, "ary-lalkyl radicals with" should be -- arylalkyl radicals which --.

Column 16,
Line 5, "formula IV" should be -- formula V --.

Signed and Sealed this

Thirtieth Day of March, 2004

JON W. DUDAS
*Acting Director of the United States Patent and Trademark Office*